(12) United States Patent
Tefft et al.

(10) Patent No.: US 10,136,986 B2
(45) Date of Patent: Nov. 27, 2018

(54) DEVICES AND METHODS FOR ENDOTHELIALIZATION OF MAGNETIC VASCULAR GRAFTS

(71) Applicant: Mayo Foundation for Medical Education and Research, Rochester, MN (US)

(72) Inventors: Brandon J. Tefft, Rochester, MN (US); Gurpreet S. Sandhu, Rochester, MN (US); Dan Dragomir-Daescu, Rochester, MN (US); Susheil Uthamaraj, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/309,630

(22) PCT Filed: May 7, 2015

(86) PCT No.: PCT/US2015/029695
§ 371 (c)(1),
(2) Date: Nov. 8, 2016

(87) PCT Pub. No.: WO2015/171897
PCT Pub. Date: Nov. 12, 2015

(65) Prior Publication Data
US 2017/0181839 A1   Jun. 29, 2017

Related U.S. Application Data

(60) Provisional application No. 61/991,253, filed on May 9, 2014.

(51) Int. Cl.
*A61F 2/07* (2013.01)
*A61L 27/18* (2006.01)
(Continued)

(52) U.S. Cl.
CPC .............. *A61F 2/07* (2013.01); *A61L 27/18* (2013.01); *A61L 27/30* (2013.01); *A61L 27/507* (2013.01);
(Continued)

(58) Field of Classification Search
CPC ................................. A61F 2/07; A61F 27/54
(Continued)

(56) References Cited

U.S. PATENT DOCUMENTS

| | | | |
|---|---|---|---|
| 5,873,906 A * | 2/1999 | Lau ........................ | A61F 2/07 128/898 |
| 8,465,453 B2 | 6/2013 | Sandhu et al. | |

(Continued)

FOREIGN PATENT DOCUMENTS

| WO | WO 2011/149913 | 12/2011 |
|---|---|---|
| WO | WO 2012/103501 | 8/2012 |

OTHER PUBLICATIONS

Park et al. Inductive heating of electrospun Fe2O3/polyurethane composite mat under high-frequency magnetic field. Ceramics International 39. 2013 pp. 9785-9790. (Year: 2013).*

(Continued)

*Primary Examiner* — Cachet I Sellman
(74) *Attorney, Agent, or Firm* — Fish & Richardson P.C.

(57) ABSTRACT

Magnetic vascular grafts and methods for their use are provided herein.

9 Claims, 2 Drawing Sheets

10%PU, 60% NaCl

(51) Int. Cl.

| | | |
|---|---|---|
| *A61L 27/30* | (2006.01) | |
| *A61L 27/50* | (2006.01) | |
| *A61L 27/54* | (2006.01) | |
| *A61L 27/56* | (2006.01) | |
| *A61L 31/02* | (2006.01) | |
| *A61L 31/06* | (2006.01) | |
| *A61L 31/08* | (2006.01) | |
| *A61L 31/14* | (2006.01) | |
| *A61L 31/16* | (2006.01) | |

(52) U.S. Cl.
CPC ............... *A61L 27/54* (2013.01); *A61L 27/56* (2013.01); *A61L 31/022* (2013.01); *A61L 31/06* (2013.01); *A61L 31/082* (2013.01); *A61L 31/146* (2013.01); *A61L 31/16* (2013.01); *A61F 2210/009* (2013.01); *A61F 2240/001* (2013.01); *A61L 2300/102* (2013.01); *A61L 2400/12* (2013.01)

(58) Field of Classification Search
USPC ................................. 427/2.24, 2.25
See application file for complete search history.

(56) References Cited

U.S. PATENT DOCUMENTS

| | | | |
|---|---|---|---|
| 8,544,474 B2 | 10/2013 | Sandhu et al. | |
| 9,468,516 B2 | 10/2016 | Sandhu et al. | |
| 2006/0167540 A1* | 7/2006 | Masters | A61F 2/90 623/1.44 |
| 2006/0239907 A1* | 10/2006 | Luzzi | A61K 49/0002 424/1.11 |
| 2008/0033233 A1* | 2/2008 | Jensen | A61F 2/06 600/36 |
| 2008/0147177 A1* | 6/2008 | Scheuermann | A61L 27/30 623/1.42 |
| 2009/0030504 A1* | 1/2009 | Weber | A61L 31/022 623/1.42 |
| 2013/0018220 A1 | 1/2013 | Vad et al. | |
| 2013/0122248 A1 | 1/2013 | Rowe | |
| 2013/0238086 A1 | 9/2013 | Ballard et al. | |
| 2013/0245748 A1 | 9/2013 | Richter | |

OTHER PUBLICATIONS

Singh et al. Potential of Magnetic Nanofiber Scaffolds with Mechanical and Biological Properties Applicable for Bone Regeneration. PLoS One. 9(4). Apr. 4, 2014 (Year: 2014).*

Lee et al. Controlling the porosity of electrospun PCL scaffold by simultaneous salt releasing method. Abstract #677 Society of Biomaterials. (Year: 2013).*

Gorna et al., "Biodegradable porous polyurethane scaffolds for tissue repair and regeneration," *J Biomed Mater Res A.*, 79A(1):128-138, Oct. 2006.

Heijkants et al., "Polyurethane scaffold formation via a combination of salt leaching and thermally induced phase separation," *J Biomed Mater Res A*, 87A(4):921-932, Dec. 15, 2008.

Heijkants et al., "Preparation of a polyurethane scaffold for tissue engineering made by a combination of salt leaching and freeze-drying of dioxane," *J Mater Sci*, 41(8):2423-2428, Apr. 2006.

Hou et al., "Porous polymeric structures for tissue engineering prepared by a coagulation, compression moulding and salt leaching technique," *Biomaterials*, 24:1937-1947, 2003.

International Preliminary Report on Patentability in International Application No. PCT/US2015/029695, dated Nov. 24, 2016, 7 pages.

International Search Report and Written Opinion in International Application No. PCT/US2015/029695, dated Aug. 7, 2015, 13 pages.

Sin et al., "Polyurethane (PU) scaffolds prepared by solvent casting/particulate leaching (SCPL) combined with centrifugation," *Mater Sci Engin C*, 30(1):78-85, Jan. 1, 2010.

* cited by examiner

FIG. 1

|  | Graft A | | Graft B | | Graft C | |
|---|---|---|---|---|---|---|
|  | lumen (μm) | cross section (μm) | lumen (μm) | cross section (μm) | lumen (μm) | cross section (μm) |
|  | 40.2 | 87.5 | 44.1 | 66.4 | 44.9 | 59.6 |
|  | 73 | 30.6 | 20.1 | 61.6 | 46.1 | 48.8 |
|  | 107 | 40 | 102 | 29.3 | 53.1 | 29.3 |
|  | 56.4 | 41.6 | 28.3 | 35.2 | 58.2 | 48.9 |
|  | 39.4 | 37.3 | 49.6 | 26.4 | 70.5 | 49.4 |
|  | 46.9 | 49.6 | 49 | 31.5 | 77.2 | 51.5 |
|  | 19.9 | 45.4 | 43.3 | 72.5 | 77.7 | 42.2 |
| Average | 54.7 | 47.4 | 48.1 | 46.1 | 61.1 | 47.1 |
| Max | 107 | 87.5 | 102 | 72.5 | 77.7 | 59.6 |
| Min | 19.9 | 30.6 | 20.1 | 26.4 | 44.9 | 29.3 |

10%PU, 70% NaCl

15%PU, 70% NaCl

10%PU, 60% NaCl

15%PU, 60% NaCl

DEVICES AND METHODS FOR ENDOTHELIALIZATION OF MAGNETIC VASCULAR GRAFTS

CROSS-REFERENCE TO RELATED APPLICATIONS

This application is a National Stage application under 35 U.S.C. § 371 of International Application No. PCT/US2015/029695, having an International Filing Date of May 7, 2015, which claims benefit of priority from U.S. Provisional Application Ser. No. 61/991,253, filed on May 9, 2014. The disclosures of the prior applications are considered part of (and are incorporated by reference in) the disclosure of this application.

TECHNICAL FIELD

This document relates to magnetic vascular grafts, and methods for their use.

BACKGROUND

Coronary bypass surgery requires the use of vascular grafts, which can be taken from autologous vessels or can be synthetic. Synthetic vascular grafts cannot be used to bypass or replace small-diameter vessels, however, due to the risk of blood clot and/or scar tissue formation.

SUMMARY

This document is based at least in part on the development of vascular grafts, and methods for making vascular grafts, that have magnetic and porous properties to attract and culture cells, thus promoting endothelialization of the grafts. Coating the inside of a graft with cells can reduce the risk of clotting and scar tissue formation.

In one aspect, this document features a method for making a porous, magnetic device. The method can include providing a solvent containing an uncured polymer, a porogen, and a magnetic substance, providing an elongate mandrel having a length of at least about 3 cm and a diameter of about 100 µm to about 3 mm, dipping at least a portion of the mandrel into the solvent containing the polymer, porogen, and magnetic substance, curing the polymer, and removing the porogen. The polymer can be, for example, polyurethane. The porogen can be sodium chloride, and the magnetic substance can be cobalt-chrome. The solvent can be dimethylacetamide. The method can further include repeating the dipping and curing steps one or more times. The method can further include winding a thread around the device after a curing step, and subsequently repeating the dipping and curing steps. The thread can include, for example, polypropylene (e.g., the thread can be a polypropylene suture thread).

In another aspect, this document features a method for making a porous, magnetic device. The method can include providing a nanofiber mesh, using electrospinning to deposit the mesh onto a rotating elongate mandrel, where the mandrel has a length of at least about 3 cm and a diameter of about 10 µm to about 100 µm, and incorporating a magnetic substance into the deposited mesh. The nanofiber mesh can be a polyurethane mesh. The magnetic substance can be cobalt-chrome. The method can further include incorporating a porogen (e.g., sodium chloride) into the nanofiber mesh.

In another aspect, this document features a method for making a magnetic stent-graft, where the method includes depositing one or more layers of material inside and/or outside of a magnetic stent. The depositing can include electrospinning. The one or more layers of material can include polyurethane. The magnetic stent can include stainless steel.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a table providing cross sectional measurements and lumen diameter measurements along the length of three exemplary grafts (Graft A, Graft B, and Graft C) as provided herein.

DETAILED DESCRIPTION

Figure 2B:
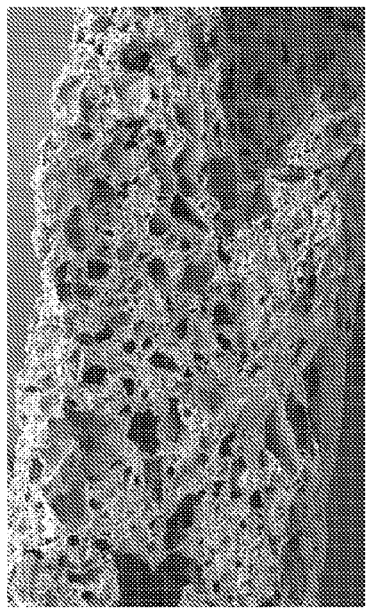
FIGS. 2A-2D are pictures of the walls of grafts having varying degrees of porosity due to their composition.

Implanted medical devices that include surfaces in contact with a patient's bloodstream can present risks that include, for example, acute thrombosis and chronic instability (e.g., calcification) of the implant surface. One approach that has been used to reduce these problems is "endothelial seeding," which places viable endothelial cells onto the blood contacting surface of a device (e.g., the lumen surface of a vascular graft, to mimic the surface of natural blood vessels). This surface modification can produce a confluent, biologically active surface of viable endothelial cells which, by definition, is anti-thrombogenic.

This document provides grafts for vascular use, as well as methods for making the grafts. The grafts can have any or all of the following characteristics and abilities:
porous
magnetic
suitable wall thickness
suturable
resistance to kinking
compliant; and
strong.

The grafts provided herein can be used to maintain patency of the vessels into which they are placed, and can have improved blood compatibility and overall graft performance as compared to other grafts (e.g., non-porous and/or non-magnetic grafts). In addition, the grafts can promote endothelialization at their site of placement, thus reducing the risks of blood clot and/or scar tissue formation. In particular, the grafts can have surfaces to which viable biological cells are magnetically attracted and retained. Thus, in some embodiments, methods for using the grafts provided herein can include attraction and retention of magnetically labelled cells to the magnetic grafts. In some embodiments, the magnetic vascular grafts can attract and capture magnetically-labeled therapeutic compounds, which also may be used to improve blood compatibility and overall graft performance.

The grafts provided herein can be made from any suitable material, including polymers such as polyurethane (PU), poly(lactic acid), poly(l-lactic acid), poly(glycolic acid), poly(lactic-co-glycolic acid), poly(glycerol sebacate), and polycaprolactone, as well as polyethylene terephthalate (DACRON®) and expanded polytetrafluoroethylene (GORE-TEX®). The grafts can be rendered magnetic by incorporating a compound such as cobalt-chrome (CoCr; also referred to as cobalt-chromium), a metal alloy of cobalt and chromium. In some embodiments, the grafts can be rendered magnetic by incorporating one or more of permalloy, 420 stainless steel, and 2205 stainless steel. The porosity of the grafts provided herein can result from the use of a porogen such as sodium chloride (NaCl) during the manufacturing process. In some embodiments, however, a porogen is not necessary to generate a porous graft. See, e.g., US2013/0018220, US2013/0122248, which are incorporated herein by reference in their entirety.

The vascular grafts provided herein are generally tubular, having a cylindrical body with a first end and a second end, and a lumen extending between the first and second ends to permit blood flow after placement in a patient. A graft can have any suitable dimensions. For example, a graft can have a length of about 0.5 cm to about 10 cm (e.g., about 0.5 to 1 cm, about 1 to 1.5 cm, about 1.5 to 2 cm, about 2 to 2.5 cm, about 2.5 to 3 cm, about 3 to 3.5 cm, about 3.5 to 4 cm, about 4 to 4.5 cm, about 4.5 to 5 cm, about 5 to 6 cm, about 6 to 7 cm, about 7 to 8 cm, about 8 to 9 cm, about 9 to 10 cm, or about 10 cm). The diameter of the lumen can vary along the length of the graft, but in general the diameter of the lumen can be about 100 µm to about 6 mm (e.g., about 100 to 250 µm, about 250 to 500 µm, about 500 to 750 µm, about 750 µm to 1 mm, about 1 to 1.5 mm, about 1.5 to 2 mm, about 2 to 2.5 mm, about 2.5 to 3 mm, or about 3 mm). Further, the grafts can have a wall thickness of about 5 µm to about 1 mm (e.g., about 5 to 10 µm, about 10 to 15 µm, about 15 to 20 µm, about 20 to 25 µm, about 25 to 100 µm, about 100 to 500 µm, about 500 to 750 µm, or about 750 µm to 1 mm). FIG. 1 provides cross section and lumen diameter measurements at various points along the length of three different graft preparations (A, B, and C).

The porosity of a graft can be controlled or modified by varying the amount of PU, NaCl, and solvent in the slurry from which the graft is formed. For example, a solvent mixture can contain about 5% to about 25% PU (e.g., about 5 to 10%, about 10 to 15%, about 15 to 20%, about 20 to 25%, or about 25% PU), and about 50% to about 80% NaCl (e.g., about 50 to 55%, about 55 to 60%, about 60 to 65%, about 65 to 70%, about 70 to 75%, about 75 to 80%, or about 80% NaCl). Controlling the porosity can be vital for graft optimization. NaCl can be ground, sieved into a certain diameter range (e.g., about 10 µm to about 100 µm), and mixed into a slurry of PU, CoCr, and solvent. After curing of the PU polymer and leaching of the NaCl porogen, a porous graft is formed.

Figure 2D:
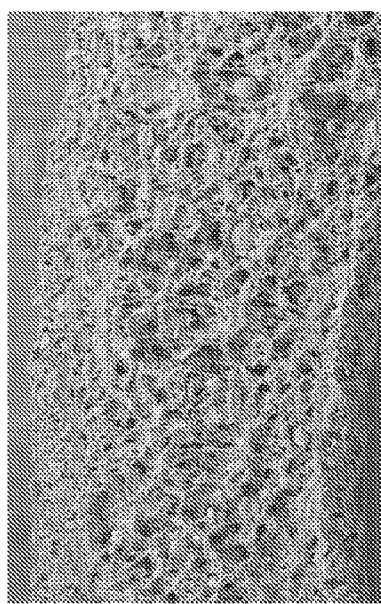
Figure 2A:
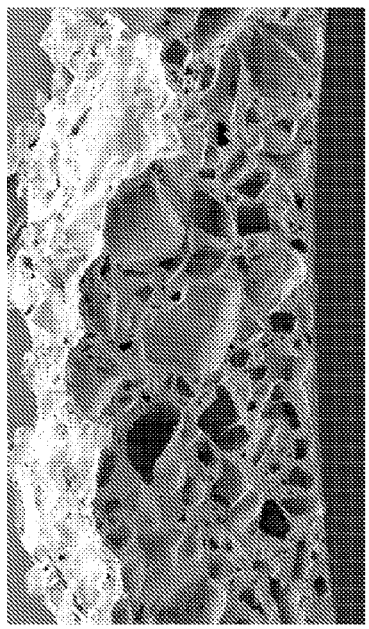
Figure 2C:
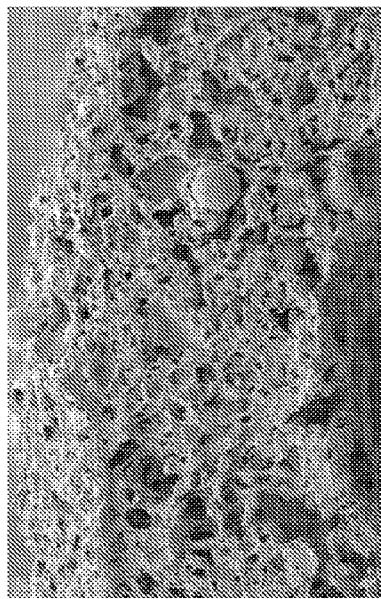

The porosity of a graft can be measured using, for example, a computer program that converts photos into binary images, and then calculates porosity. Exemplary photos of porous grafts made by the methods provided herein are shown in FIGS. 2A-2D. The grafts were made with 10% PU and 60% NaCl (FIG. 2A), 10% PU and 70% NaCl (FIG. 2B), 15% PU and 60% NaCl (FIG. 2C), or 15% PU and 70% NaCl (FIG. 2D).

Any suitable method can be used to fabricate the grafts provided herein. In some embodiments, for example, grafts can be produced by dipping at least a portion of an elongate mandrel into a viscous solution of PU, NaCl, and CoCr in a solvent (e.g., dimethylacetamide (DMA); $CH_3C(O)N(CH_3)_2$). The graft can be cured as the DMA evaporates, leaving behind a solid mixture of PU, NaCl, and CoCr. Multiple layers can be dipped and cured to achieve a desired wall thickness. Once the desired all thickness is achieved, the NaCl can be leached out, leaving behind a porous solid mixture of PU and CoCr.

The elongate mandrel can be essentially cylindrical, with any suitable dimensions. For example, a mandrel can have a length of at least about 3 cm (e.g., at least 3 cm, at least 4 cm, at least 5 cm, at least 6 cm, at least 7 cm, or at least 8 cm). The diameter of the mandrel will determine the diameter of the lumen of the grafts that will be formed thereon. Thus, the mandrel can have a diameter of about 100 µm to about 3 mm (e.g., about 100 to 250 µm, about 250 to 500 µm, about 500 to 750 µm, about 750 µm to 1 mm, about 1 to 1.5 mm, about 1.5 to 2 mm, about 2 to 2.5 mm, about 2.5 to 3 mm, or about 3 mm).

In some embodiments, the grafts provided herein can be fabricated to be resistant to kinking. Grafts with low kink resistance can develop sharp bends, causing the grafts to fail at a specific radius. In some embodiments, the kink resistance of the grafts provided herein can be increased by incorporating a thread, such as a polypropylene (e.g., prolene) suture winding between at least two of the dipped layers. A magnetic wire coil also can be used to provide kink resistance, as well as to provide additional magnetic properties. The degree of kink resistance can be modulated based on the coil/cm; a specific coil/cm value can be used to allow for smaller bend radii before a sharp bend or kink develops.

In some embodiments, the grafts provided herein can be produced using electrospinning. See, e.g., WO2012/103501, US2013/0238086, US2013/0245748, US2013/0018220, and US2013/0122248, which are incorporated herein by reference in their entirety. Electrospinning can be used to generate a mesh of nanofibers (e.g., PU nanofibers), which can impart desirable mechanical and cell adhesion properties. The parameters of the electrospinning can be varied to achieve a desired degree of porosity. In some cases, a porogen such as NaCl can be used to provide porosity to an electrospun graft. Electrospun grafts can be rendered magnetic by incorporation of CoCr (e.g., CoCr powder). Further, an electrospinning graft preparation process can include the step of incorporating a thread (e.g., a polypropylene suture) into the graft to increase its kink resistance.

Electrospinning also can be used to fabricate magnetic stent-grafts. For example, a magnetic stent-graft can be been generated by electrospinning one or more layers of a polymer (e.g., PU) inside and/or outside of a magnetic stent (e.g., a magnetic stent comprising a material such as stainless steel). Such a device can be crimped to a diameter suitable for percutaneous delivery into the vascular system. Any suitable magnetic material can be used to fabricate the stent (e.g., 2205 stainless steel, 420 stainless steel, cobalt chromium, or permalloy), and any suitable material can be layered on the inner and/or outer surface of the stent. Useful layering materials include, without limitation, polymers such as polyurethane, polyethylene terephthalate, expanded polytetrafluoroethylene, polycaprolactone, poly(lactic acid), poly(l-lactic acid), poly(glycolic acid), poly(lactic-co-glycolic acid), and poly(glycerol sebacate), as well as collagen.

As alternatives or in addition to electrospinning, methods for making such magnetic stent grafts can include solvent casting, electrospraying, and/or weaving, for example.

Once placed, a stent-graft can act as an intraluminal graft with cell capture and cell adhesion properties. Such devices can be used to, for example, cover small tears in blood vessels to stop hemorrhaging, to act as a flow diverter for treating aneurysms by keeping the flow confined to the blood vessel, thus diverting it away from the aneurysm bleb/injury, or to act as a normal stent with enhanced biocompatibility and bio-integration, promoted by the electrospun nanofiber scaffold around the stent structure.

In use, the magnetic, porous grafts as provided herein can attract and retain biological cells having a magnetic label. In some embodiments, for example, a pharmacologically acceptable carrier containing a population of magnetically labelled cells can be delivered to the vicinity of a magnetic graft placed in a vessel, such that the cells become associated with the graft surface(s). In other embodiments, biological cells can be magnetically attached to an implantable medical device in vitro, by placing a magnetic graft as provided herein in a carrier liquid containing a plurality of magnetically-labeled cells, where a plurality of the plurality of magnetically labelled cells are magnetically attracted to and retained on the implantable medical device. The graft and the cells then can be implanted in a vessel. See, e.g., U.S. Pat. Nos. 8,465,453 and 8,544,474, which are incorporated herein by reference in their entirety.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making a porous, magnetic device consisting of a cured polymer and a magnetic substance and, optionally, a thread wound around the device, the method comprising:
   providing a solvent containing an uncured polymer, a porogen, and a magnetic substance;
   providing an elongate mandrel having a length of at least about 3 cm and a diameter of about 100 µm to about 6 mm;
   dipping at least a portion of the mandrel into the solvent containing the polymer, porogen, and magnetic substance;
   curing the polymer; and
   removing the porogen.

2. The method of claim 1, wherein the polymer is polyurethane.

3. The method of claim 1, wherein the porogen is sodium chloride.

4. The method of claim 1, wherein the magnetic substance is cobalt-chrome.

5. The method of claim 1, wherein the solvent is dimethylacetamide.

6. The method of claim 1, further comprising repeating the dipping and curing steps one or more times.

7. The method of claim 1, further comprising winding a thread around the device after a curing step, and subsequently repeating the dipping and curing steps.

8. The method of claim 7, wherein the thread comprises polypropylene.

9. The method of claim 8, wherein the thread is a polypropylene suture thread.

* * * * *